United States Patent
Ganton et al.

(10) Patent No.: US 10,062,958 B2
(45) Date of Patent: Aug. 28, 2018

(54) WEARABLE ELECTRONIC PATCH WITH ANTENNA ENHANCEMENT

(71) Applicant: QUALCOMM Incorporated, San Diego, CA (US)

(72) Inventors: Robert Bruce Ganton, San Diego, CA (US); Robert Scott Ballam, Eatons Hill (AU)

(73) Assignee: QUALCOMM Incorporated, San Diego, CA (US)

( * ) Notice: Subject to any disclaimer, the term of this patent is extended or adjusted under 35 U.S.C. 154(b) by 951 days.

(21) Appl. No.: 14/550,318

(22) Filed: Nov. 21, 2014

(65) Prior Publication Data
US 2016/0149292 A1    May 26, 2016

(51) Int. Cl.
*H05K 5/00*    (2006.01)
*G11B 33/02*    (2006.01)
(Continued)

(52) U.S. Cl.
CPC .......... *H01Q 1/273* (2013.01); *A61B 5/0022* (2013.01); *A61B 5/01* (2013.01); *A61B 5/02438* (2013.01); *A61B 5/0402* (2013.01); *A61B 5/14532* (2013.01); *A61B 5/6832* (2013.01); *A61B 5/6833* (2013.01); *A61B 5/6844* (2013.01); *G06K 19/0716* (2013.01); *G06K 19/0718* (2013.01); *G06K 19/0723* (2013.01); *G06K 19/07771* (2013.01); *G06K 19/07773* (2013.01); *H01Q 9/04* (2013.01); *H05K 3/30* (2013.01); *A61B 5/02141* (2013.01); *A61B 5/0478* (2013.01); *A61B 5/0531* (2013.01); *A61B 5/1455* (2013.01); *A61B 5/1468* (2013.01); *A61B 5/4839* (2013.01);

(Continued)

(58) Field of Classification Search
CPC .................................................. A61B 5/14552
USPC ..................................................... 361/679.01
See application file for complete search history.

(56) References Cited

U.S. PATENT DOCUMENTS 5,862,803 A *   1/1999   Besson .............. A61B 5/14552
                                                              128/903
7,450,077 B2   11/2008   Waterhouse et al.
(Continued)

FOREIGN PATENT DOCUMENTS

WO    2009056642 A1    5/2009
WO    2013068043 A1    5/2013

OTHER PUBLICATIONS

International Search Report and Written Opinion—PCT/US2015/053723—ISA/EPO—Jan. 14, 2016.
(Continued)

*Primary Examiner* — Jerry Wu
(74) *Attorney, Agent, or Firm* — Kilpatrick Townsend & Stockton (57) ABSTRACT

A wearable electronic patch with an enhanced radio antenna includes an antenna, radio circuitry, a base portion, a distal portion, and intermediate portion, and a spacer, configured to raise the antenna away from the base portion, and thus away from a wearer to improve radiation properties of the antenna. The spacer may be sized and shaped to expand from a compressed state, as it may be when the patch is packaged, to an expanded state that raises the antenna when it is applied to a wearer. Other aspects, embodiments, and features are also claimed and disclosed.

15 Claims, 4 Drawing Sheets

(51) Int. Cl.
| | |
|---|---|
| *H01Q 1/27* | (2006.01) |
| *A61B 5/01* | (2006.01) |
| *A61B 5/024* | (2006.01) |
| *A61B 5/0402* | (2006.01) |
| *A61B 5/145* | (2006.01) |
| *A61B 5/00* | (2006.01) |
| *H01Q 9/04* | (2006.01) |
| *H05K 3/30* | (2006.01) |
| *G06K 19/07* | (2006.01) |
| *G06K 19/077* | (2006.01) |
| *A61B 5/021* | (2006.01) |
| *A61B 5/0478* | (2006.01) |
| *A61B 5/053* | (2006.01) |
| *A61B 5/1455* | (2006.01) |
| *A61B 5/1468* | (2006.01) |
| *H01Q 9/26* | (2006.01) |

(52) U.S. Cl.
CPC ....... *A61B 2503/10* (2013.01); *A61B 2503/40* (2013.01); *A61B 2560/0412* (2013.01); *A61B 2562/0257* (2013.01); *A61B 2562/12* (2013.01); *A61B 2562/166* (2013.01); *A61B 2562/182* (2013.01); *A61B 2562/187* (2013.01); *A61B 2562/242* (2013.01); *A61B 2562/247* (2013.01); *H01Q 9/26* (2013.01)

(56) References Cited

U.S. PATENT DOCUMENTS

| | | |
|---|---|---|
| 8,169,322 B1 | 5/2012 | Zhan et al. |
| 2010/0155492 A1 | 6/2010 | Forster |
| 2011/0245653 A1 | 10/2011 | Varahramyan et al. |
| 2014/0191912 A1 | 7/2014 | Darden, IV et al. |
| 2014/0319225 A1 | 10/2014 | Van Rens et al. |

OTHER PUBLICATIONS

Purohit S., et al., "A Review on Wearable—Textile Patch Antenna," International Journal of Scientific & Engineering Research, Dec 2013, vol. 4 (12), pp. 696-702.

\* cited by examiner

WEARABLE ELECTRONIC PATCH WITH ANTENNA ENHANCEMENT

BACKGROUND

Wearable medical devices may provide biometric monitoring and reporting relating to a wearer. In the case of wearable medical devices that use wireless communications, such as wearable electronic patches, there are several challenges. For example, the compact nature of a patch, the close proximity of the patch against a wearer's body, the compression force applied to the patch when the patch is pressed against the wearer's body, and the limited number of acceptable biocompatible materials that may be used for the patch may all impact the performance of wireless communications.

SUMMARY

In some aspects, a wearable electronic patch with an enhanced radio antenna may include an antenna, a base portion, a distal portion, an intermediate portion, and a spacer that is configured to expand in order to provide a gap between the antenna and the skin of a wearer. The spacer may be sized and shaped to expand from a compressed state when applied to the wearer. This may enable the electronic patch to be compact within packaging without compromising performance of the antenna.

In some aspects, when fully compressed the spacer may maintain a space between the base portion and the antenna. The spacer may be formed of a foam material configured to slowly expand after the base portion is secured to the wearer. The spacer may have a dielectric constant of approximately 1.0. The spacer may be used for patients, exercise, general body monitoring, or other applications.

BRIEF DESCRIPTION OF THE DRAWINGS

The accompanying drawings are presented to aid in the description of embodiments of the disclosure and are provided solely for illustration of the embodiments and not limitation thereof.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

Various embodiments include a wearable electronic patch with antenna enhancement. The wearable electronic patch may be a wirelessly connected topical patch worn for biological monitoring and/or reporting relating to a wearer. For example, the wearable electronic patch may be used for drug therapy and/or monitoring. The wearer may be any individual wanting and/or needing to measure biometric characteristics of interest. The antenna enhancements may improve antenna performance, reliability, and operating range of the wirelessly connected wearable electronic patch. A spacer sized and shaped to expand (i.e., resiliently biased) from a compressed state may be used to increase and/or maintain the distance of the antenna from the body of the wearer. When the wearable electronic patch, according to various embodiments, is placed on the wearer (e.g., affixed to the skin), pressure may compress the patch, including the spacer. Once the pressure is removed, the resilient spacer may expand, thereby increasing a distance of the antenna from the wearer.

The words "first" and "second," and similar terms are used herein for clarity purposes to distinguish various described elements and are not intended to limit the claims to a particular order or hierarchy of elements.

As used herein, the term "wearable electronic patch" refers to a device, in the form of a topical electronic patch, that may include sensors for sensing or measuring one or more detectable physical characteristics. A wearable electronic patch may be configured to a transmit signals indicative of a measurement or sensed state, condition, or quantity of the one or more detectable physical characteristics.

As used herein, the term "sensor" refers to a device that detects or measures a physical property and records, generates signals, or otherwise responds to the physical property. The signals generated by the sensor may be processed to measure the one or more detectable characteristics based on a correlation between the signal and the underlying quantity. Non-limiting examples of sensors that may be implemented in the wearable electronic patch include temperature sensors, pulse sensors, allergy sensors, electric field sensors (e.g., electroencephalograph sensors), moisture sensors, liquid flow sensors, level sensors, magnetic sensors, piezoelectric sensors, pressure sensors, optical sensors, chemical sensors (e.g., blood glucose sensors), skin contact/attachment detection sensors (e.g., a body detection circuit), and/or other bio-medical sensors. A body detection circuit may detect when the wearable electronic patch is worn by a wearer. In response to detecting the wearable electronic patch has been mounted on a wearer, other components may be activated. In this way, battery power may be conserved prior to use on a wearer.

As used herein, the term "wearer" refers to an entity having the wearable electronic patch on their body or a part of their body, such as applied directly to skin. The wearer may be any individual wanting and/or needing to measure biometric characteristics of interest. For example, a wearer may be a patient prescribed to wear the wearable electronic patch to administer medicine or measure biometric characteristics relative to a medical condition. As a further example, a wearer may be an athlete or fitness enthusiast wanting to measure biometric characteristics relevant to health and wellness. As yet a further example, the wearer may be an animal being tracked and/or monitored.

As used herein, the terms "antenna" or "antennae" refer to an electrical device, which converts electric power into radio waves, and vice versa. Antenna may be used with radio circuitry, such as a radio transmitter and/or radio receiver. In transmission, a radio transmitter supplies an electric current oscillating at radio frequency to the antenna's terminals, and the antenna radiates the energy from the current as electromagnetic waves (radio waves). In reception, an antenna intercepts some of the power of an electromagnetic wave in order to produce a tiny voltage at its terminals that may be applied to a receiver to be amplified. An antenna may include one or more metallic conductors, electrically connected to the receiver or transmitter.

As used herein, the term "radio circuitry" refers to one or more electronic devices used to transmit and/or receive radio signals between two devices using an antenna. Radio circuitry may include a system of circuit elements, including electrical conductors and components, in which all or some of the circuit elements are inseparably associated and electrically interconnected. In addition, the radio circuitry may be configured to operate with the antenna using one or more wireless technology standards, specifications, or protocols (e.g., Peanut®, Bluetooth®, Personal Area Network (PAN), Zigbee®, Wi-Fi, RF radio) for sending and receiving signals.

As used herein, the term "printed circuit board" refers to a structure that may mechanically support and electrically connect electronic components using conductive tracks, pads, and other features etched from conductive metal sheets laminated onto a non-conductive substrate. The printed circuit board may be flexible, rigid, or some combination thereof, including one or more portions that are flexible and one or more other portions that are rigid.

As used herein, the term "resiliently biased" refers to an element that has a tendency to expand or spring back toward a natural structural configuration and/or dimension after being compressed, bent or otherwise deformed. In this way, a spacer may be sized and shaped accordingly to provide a resilient biasing of elements.

Figure 1:
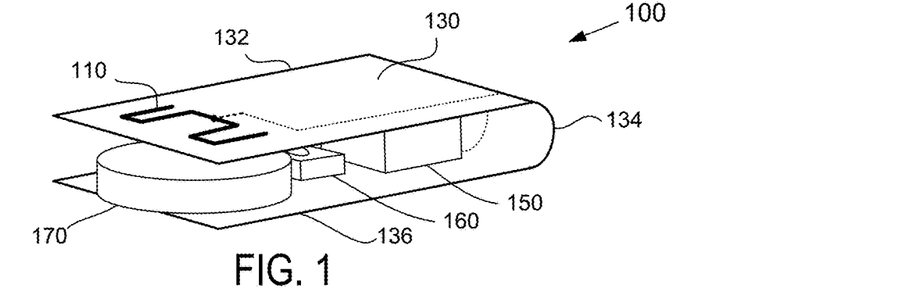
FIG. 1 is a perspective view of a wearable electronic patch in accordance with various embodiments.

FIG. 1 illustrates a perspective view of a wearable electronic patch 100 in accordance with various embodiments. The wearable electronic patch 100 may include an antenna 110 coupled to associated radio circuitry for providing wireless communications from or to the wearable electronic patch 100. The antenna 110, which may be for example a dipole antenna, may be incorporated onto or into a distal portion 132 of a printed circuit board 130. The antenna 110 may be disposed at one end of the distal portion 132, as illustrated, or may be disposed in a more central region of the distal portion 132. In an embodiment, the antenna 110 may be configured so that a spacer 150 is disposed between the antenna 110 and a base portion 136. The spacer 150 may be sized and shaped to expand and maintain the antenna 110 spaced away from the base portion 136 of the printed circuit board 130. In addition, since the base portion 136 may be closer to the wearer of the wearable electronic patch 100 than the distal portion 132, the spacer 150 may also maintain the antenna 110 spaced away from the wearer.

The wearable electronic patch 100 may include additional circuitry and/or components, such as a sensor 160 for biological monitoring. The sensor 160 may measure one or more detectable physical characteristics of the wearer and/or a substance delivered by the wearable electronic patch 100 through the skin. A medicated transdermal delivery component may be part of the sensor 160 or a separate component for delivering a compound or other substance. In this way, the wearable electronic patch 100 may include a drug delivery component attached to the base portion for delivering a drug to the wearer. The sensor 160 may be attached to the base portion 136, or be incorporated therein, to contact or be in close proximity to the wearer's skin once worn by the wearer. In an embodiment, the sensor 160 may include a body detection circuit capable of detecting when the wearable electronic patch 100 is attached to the wearer. The body detection circuit may be used to only allow power from a battery 170 to be drawn in response to determining the wearable electronic patch 100 is attached to the wearer.

Figure 2A:
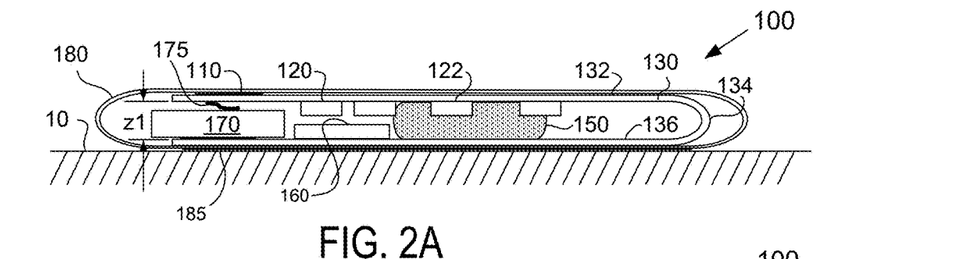
FIG. 2A is a side elevation view of a wearable electronic patch in a compressed state worn by a wearer in accordance with various embodiments.

The wearable electronic patch 100 may include the battery 170 for powering one or more of the various components of the wearable electronic patch 100. For example, the battery 170 may supply power to the antenna 110 and/or the sensor 160. The battery 170 may be a button cell battery, shaped as a squat cylinder with a thin profile. In this way, the battery 170 may be at least partially disposed between the base portion and the distal portion. The battery 170 may be coupled to the printed circuit board 130 and/or directly connected to particular components. As shown in FIG. 2A, for example, one or more contacts 175 may be provided for engaging terminals of the battery 170. In an embodiment, the contacts 175 may be biased to maintain engagement with the battery 170, regardless of the distance between the distal portion 132 and the base portion 136. In addition, the battery 170 may be configured to be secured in the wearable electronic patch 100, as a replaceable component (i.e., removably secured), or permanently secured therein.

Figure 2B:
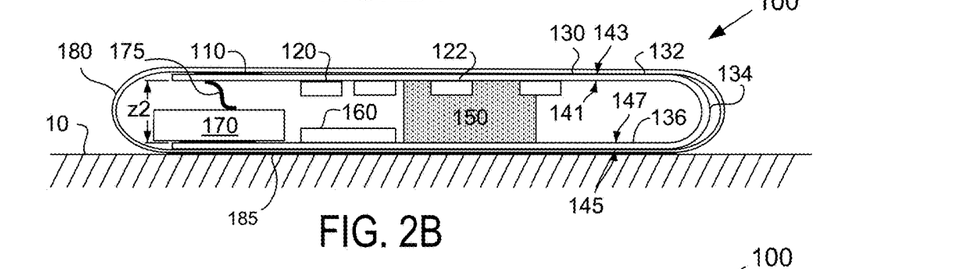
FIG. 2B is a side elevation view of a wearable electronic patch in an expanded state worn by a wearer in accordance with various embodiments.

FIGS. 2A-2B illustrate side elevation views of the wearable electronic patch 100 worn by a wearer 10 in two stages of compression, in accordance with various embodiments. The wearable electronic patch 100 may be provided with a permanent packaging 180, which may be secured directly to a contact surface of the wearer 10, such as the wearer's skin or an intermediate material, by a removable adhesive 185 on one side of the wearable electronic patch 100.

The side elevation views of FIGS. 2A-2B also show the configuration of various elements of the wearable electronic patch 100. For example, three portions of the printed circuit board 130 are distinguished for reference purposes, namely the distal portion 132, an intermediate portion 134, and the base portion 136. The base portion 136 may be configured to be closest to the wearer 10. The intermediate portion 134 may join the distal portion 132 to the base portion 136.

FIG. 2A illustrates the wearable electronic patch 100 in a compressed state, such as when pressure is applied (e.g., the wearable electronic patch 100 is pressed against the wearer 10). The wearer 10 or another person may press the wearable electronic patch 100 onto the contact surface of the wearer 10 (e.g., bare skin) to allow the removable adhesive 185 to attach to the wearer 10. Pressure applied to the wearable electronic patch 100, may compress/deform the overall structure resulting in the structure being, at least temporarily, in a compressed state. Compression of the wearable electronic patch 100 may also compress the spacer 150.

FIG. 2B illustrates the wearable electronic patch 100 in an un-compressed state, such as when pressure is removed or less pressure is applied. For example, once firmly secured to the wearer 10, the application of pressure may be relieved from the wearable electronic patch 100 allowing expansion thereof. The spacer 150, which is sized and shaped to expand from a compressed state, may expand when the pressure is relieved, thereby moving the distal portion 132, including the antenna 110, away from the base portion 136.

The spacer may be sized and shaped to enable or provide a number of arrangements for the wearable electronic patch 100. For example, a z-height may define a distance between the distal portion 132 and the base portion 136. A compressed z-height z1 (e.g., FIG. 2A) may be smaller than a lesser-compressed z-height z2 (e.g., FIG. 2B). For example, the compressed z-height z1 may be less than 2 mm, while the lesser-compressed z-height z2 may be 2.0-2.5 mm or more. A z-height of approximately 2.0-2.5 mm may achieve suitable operation for the antenna 110 and a marked improvement from operations in the compressed state. In an embodiment, the spacer 150 through selection of materials and/or size may have a compression limit for maintaining a minimum space (i.e., a minimum z-height) between the base portion 136 and the distal portion 132, including the antenna 110. For example, compressed z-height z1 may be a minimum z-height. In an embodiment, internal components of the wearable electronic patch 100 may limit and define the minimum z-height. Such internal components may include radio circuitry 120, a processor 122, the sensor 160, the battery 170, and additional components.

The spacer 150 may be formed of a material configured to maintain a reliable and effective z-height. In this way, once pressure maintaining the spacer 150 compressed is released, the spacer 150 may slowly expand (i.e., gradually, rather than quickly or suddenly). In addition, the spacer 150 may be formed of appropriate biocompatible materials for application to the wearer 10. Since the spacer 150 is in close proximity to the antenna 110, a dielectric constant of the material(s) forming the spacer 150 may be selected to be approximately 1.0 or as close to 1.0 as possible in order to minimize interference. The spacer 150 may effectively be invisible to the antenna 110 if the spacer 150 has a dielectric constant of approximately 1.0. Otherwise, as a dipole antenna, an adjacent dielectric material having a dielectric constant greater than 1.0 may make the ground plane operate as if it were closer to the radiating element, which may affect the performance of the antenna 110.

The base portion 136 of the wearable electronic patch 100 may have a lower surface 145 configured to face the wearer 10, such as toward a portion of the wearer's skin. The permanent packaging 180 may be interposed between the lower surface 145 and the wearer 10. In some embodiments, the removable adhesive 185 may be applied when placing the wearable electronic patch 100 on the wearer 10. In this way, the removable adhesive may be included outside the permanent packaging 180, also on the side facing the wearer 10. In some embodiments, the removable adhesive 185 may be an adhesive tape secured to the permanent packaging 180, with a peel away protection layer removed prior to installation. The removable adhesive 185 may firmly secure the wearable electronic patch 100 to the wearer 10, while still being easily removable later when desired.

An upper surface 147 of the base portion 136 may face a lower surface 141 of the distal portion 132. Also, the distal portion 132 may have an upper surface 143 opposed to the lower surface 141. A first end of the intermediate portion 134 may be attached to the distal portion 132 and a second end of the intermediate portion 134 may be attached to the base portion 136. In this way, the intermediate portion 134 may be folded over itself so that the distal portion 132 may extend parallel to, or substantially parallel to, the base portion 136. The distal portion 132, the intermediate portion 134, and the base portion 136 may form a continuous printed circuit board.

Figure 3:
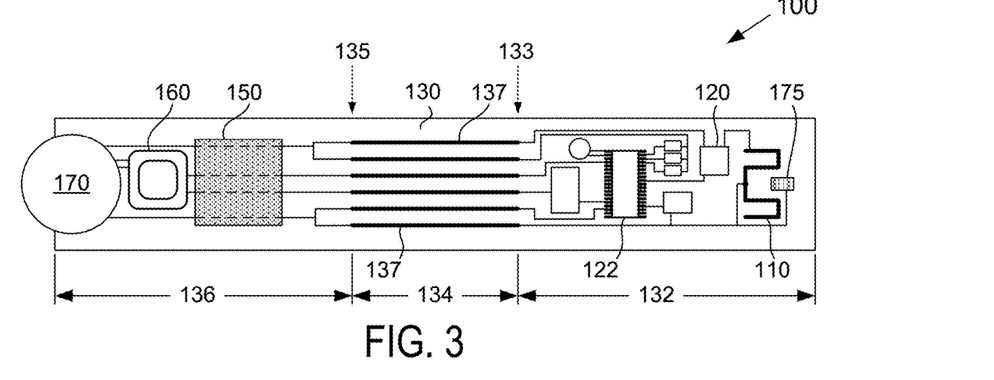
FIG. 3 is an unfolded plan view of a wearable electronic patch in accordance with various embodiments.

FIG. 3 illustrates an unfolded plan view of a wearable electronic patch 100 in accordance with various embodiments. Various components may be assembled onto and/or into the printed circuit board 130 in a planar state. Once assembled, the printed circuit board 130 may be folded, such as by using a web conversion process. For example, a first end 133 of the intermediate portion 134 attached to the distal portion 132 may be folded over a second end 135 of the intermediate portion 134 attached to the base portion 136.

The antenna 110 may be a circuit element printed onto the distal portion 132. The antenna 110 may be incorporated into and/or integrally formed with the printed circuit board 130. In some embodiments, the antenna 110 may be a circuit component printed directly onto a surface of the printed circuit board 130. The antenna 110 may be printed onto the lower surface (e.g., 141 in FIG. 2B) or the upper surface (e.g., 143 in FIG. 2B) of the distal portion 132. In some embodiments, the antenna 110 may be integrally formed as a laminate inner or outer layer of the printed circuit board 130. In some embodiments, the antenna 110 may be a dipole antenna. Various other components, such as radio circuitry 120, processor 122, the contact 175, and additional components may be mounted on the distal portion 132. The battery 170 may be used as part of or an extension of the antenna 110. In addition, the spacer 150 may isolate the electronics from the sensor 160, which may be a capacitive sensor for body detection circuitry.

In an embodiment, the whole of the printed circuit board 130 is formed of a single continuous material or laminate structure. In an embodiment, the distal portion 132 and/or the base portion 136 may be more or less flexible than the intermediate portion 134. The intermediate portion 134 may include conductive elements 137 extending along a longitudinal extent of the printed circuit board 130. The conductive elements 137 may couple components (e.g., 110, 120, 122, 175) on the distal portion 132 to other components (e.g., 150, 160, 170) on the base portion 136.

Figure 4:
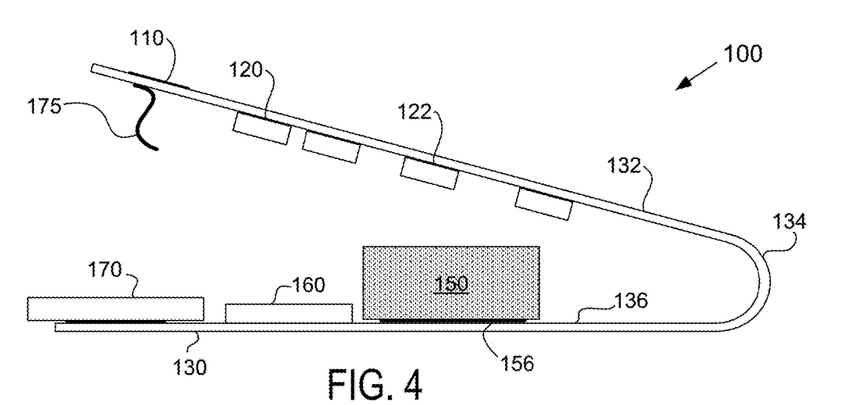
FIG. 4 is a side elevation view of the wearable electronic patch of FIG. 3 being folded in accordance with various embodiments.

FIG. 4 illustrates a side elevation view of the wearable electronic patch 100 of FIG. 3 folded in accordance with various embodiments. As part of assembling the wearable electronic patch 100, the distal portion 132 may be folded over the base portion 136. The various components (e.g., the antenna 110, the radio circuitry 120, the processor 122, and the contact 175) may be firmly secured to the distal portion 132, such as through soldering, ensuring they remain in place when folding the printed circuit board 130. The sensor 160 may be built into or firmly secured to the base portion 136. In addition, a lower adhesive layer 156 may secure the spacer 150 to the base portion 136. Similarly, a conductive adhesive (not shown) may secure the battery 170 to the distal portion 132.

Figure 5:
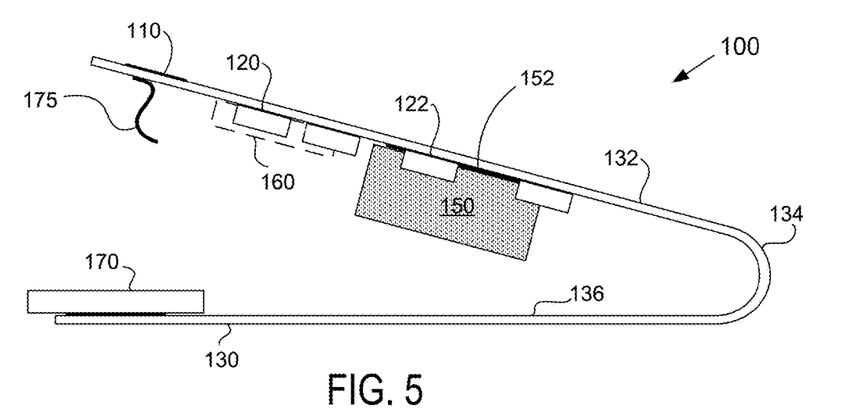
FIG. 5 is a side elevation view of a wearable electronic patch being folded in accordance with various embodiments.

FIG. 5 illustrates a side elevation view of the wearable electronic patch 100 being assembled with the spacer 150 and optionally the sensor 160 initially affixed to the distal portion 132, in accordance with various embodiments. The sensor 160 may also benefit from being spaced away from the base portion 136, similar to the antenna 110 by being mounted on the distal portion. For example, by separating the sensor from other circuitry of the electronic patch (e.g., radio circuitry 120) the sensitivity or accuracy of the sensor may be improved by reducing an amount of electronic noise and/or heat generated from other circuits of the patch.

An upper adhesive layer 152 may secure the spacer 150 to the distal portion 132. As a further alternative, the spacer 150 need not be secured to either the distal portion 132 or the base portion 136 using an adhesive, but rather may be held in place by being sandwiched between the distal portion 132 and the base portion 136. A seat or guides (not shown) may secure the spacer 150 from moving out of place once the spacer 150 is sandwiched between the distal portion 132 and the base portion 136.

Figure 6:
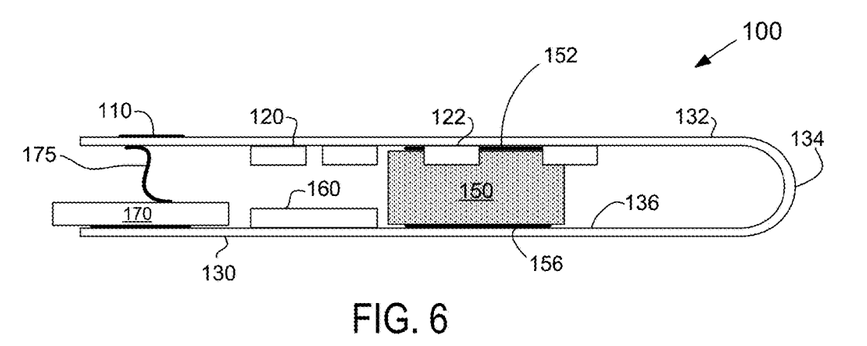
FIG. 6 is a side elevation view of a wearable electronic patch folded in accordance with various embodiments.

FIG. 6 illustrates a side elevation view of a wearable electronic patch completely folded in accordance with various embodiments. In this way, once the printed circuit board 130 is folded, the various components, such as the antenna 110, the radio circuitry 120, the processor 122, the spacer 150, the sensor 160, the battery 170, and/or the contact 175 may be disposed between the base portion and the distal portion. In an embodiment, both the upper adhesive layer 152 and the lower adhesive layer 156 may secure the spacer within the wearable electronic patch 100. In addition, using both the upper adhesive layer 152 and the lower adhesive layer 156 may limit a distance the distal portion 132 may move away from the base portion 136. Alternatively, the spacer may be mechanically secured using mechanical fasteners or through structural elements of the spacer 150 that interlock with the distal portion 132 and/or the base portion 136. The sensor 160 may be secured to the base portion 136, when the sensor 160 is a body or drug detection component, like a capacitive touch or temperature sensor. The sensor 160 may benefit from being placed on the opposite side of the printed circuit board 130 from the other electronic elements, such as the antenna 110, the radio circuitry 120, and the processor 122. In this way, the spacer 150 may ensure that any interaction between the sensor 160 and the other electronic elements is minimized. Persons skilled in the art will appreciate that one or more of the radio circuitry 120, the processor 122, and additional components may be secured to and/or mounted on the base portion 136.

Figure 7:
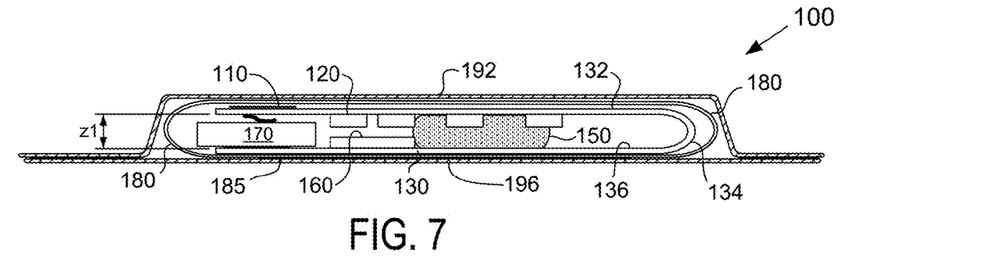
FIG. 7 is a side elevation view of a wearable electronic patch in packaging in accordance with various embodiments.

FIG. 7 illustrates a side elevation view of a wearable electronic patch 100 in the permanent packaging 180 in accordance with various embodiments. The wearable electronic patch 100 may be provided with temporary packaging layers 192, 196. The permanent packaging 180 may be a thin flexible substrate sized to encase all or most of the wearable electronic patch 100. By fully enveloping, and thereby encasing, the entire wearable electronic patch 100, the permanent packaging 180 may ensure water and/or other contaminants do not interact with or compromise the wearable electronic patch 100. Alternatively, the permanent packaging 180 may have a gap or other open region exposing a lower region of the wearable electronic patch 100. That lower region of the wearable electronic patch 100 not covered by the permanent packaging 180 may include the removable adhesive 185. In this way, the removable adhesive 185 may affix the base portion 136 to the wearer, while the permanent packaging 180 may cover at least one of the distal portion 132, the intermediate portion 134, and the base portion 136. In addition, the permanent packaging 180 may loosely envelop the wearable electronic patch 100, allowing expansion thereof. The permanent packaging 180 may be flexible enough to compress and expand along with the elements of the wearable electronic patch 100.

The wearable electronic patch 100 may also be provided with temporary packaging layers 192, 196. The temporary packaging layers 192, 196 may seal and protect the wearable electronic patch 100 until it is ready for use. An upper temporary packaging layer 192 may include a mild adhesive so it may mildly stick to an outer portion of the permanent packaging 180. In this way, the upper temporary packaging layer 192 may be peeled away when applying the wearable electronic patch 100 to the wearer. In addition, a lower temporary packaging layer 196 may include a waxy film preventing it from sticking to the removable adhesive 185.

Peripheral edges of the temporary packaging layers 192, 196 may be attached together in such a way that they may be easily separated by peeling them apart. In addition, an adhesion strength holding together the peripheral edges may be strong enough to hold the wearable electronic patch 100 in a compressed state, such as for shipping, which is reflected by a compressed z-height z1 (i.e., a compressed state).

Figure 8:
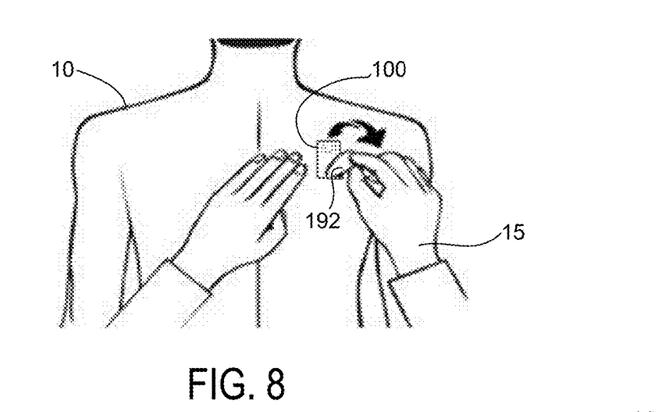
FIG. 8 is a plan view of a wearable electronic patch being applied to a wearer as a medical sensor patch in accordance with various embodiments.

FIG. 8 illustrates a plan view of the wearable electronic patch 100 being applied to a wearer 10, as a medical sensor patch by another individual 15, in accordance with various embodiments. The wearer may be prepared for receiving wearable electronic patch 100. Preparation may include pulling away and/or removing clothes, cleaning the skin, and generally clearing the area where the wearable electronic patch 100 will be applied. The lower temporary packaging layer 196 may be removed, exposing the removable adhesive 185. The wearable electronic patch 100 may be pressed against the wearer's skin, with the removable adhesive 185 disposed between the wearable electronic patch 100 and the wearer 10. The removable adhesive 185 on the underside of the medical device may hold the medical device in place. Pressing the wearable electronic patch 100 against the wearer's skin may allow the removable adhesive 185 to set and adhere to the wearer 10. With the wearable electronic patch 100 affixed to the wearer 10; the upper temporary packaging layer 192 may be peeled away as illustrated.

Figure 9:
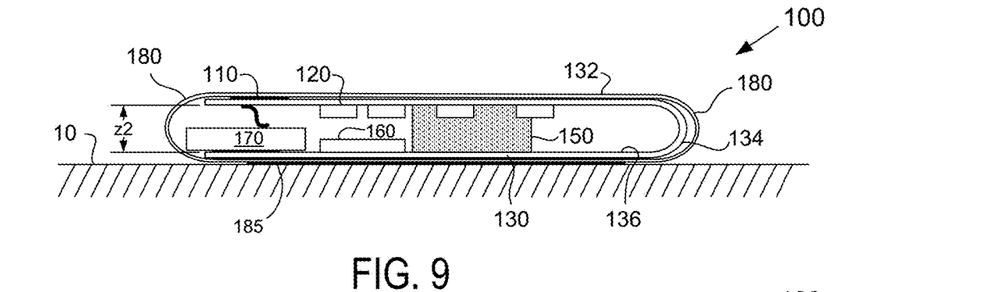
FIG. 9 is a side elevation view of a wearable electronic patch worn by a wearer in accordance with various embodiments.

FIG. 9 illustrates a side elevation view of the wearable electronic patch 100, with permanent packaging 180, worn by the wearer 10, in accordance with various embodiments. With the temporary packaging layers 192, 196 removed, the spacer 150 is released and allowed to expand from a first state (e.g., the compressed state, see FIG. 7) to a second state (i.e., a lesser-compressed state), which is reflected by the lesser-compressed z-height z2. The lesser-compressed state may be a fully uncompressed state or less than fully uncompressed state. The permanent packaging 180 may envelop the wearable electronic patch 100 less loosely once the temporary packaging layers 192, 196 are removed.

Figure 10:
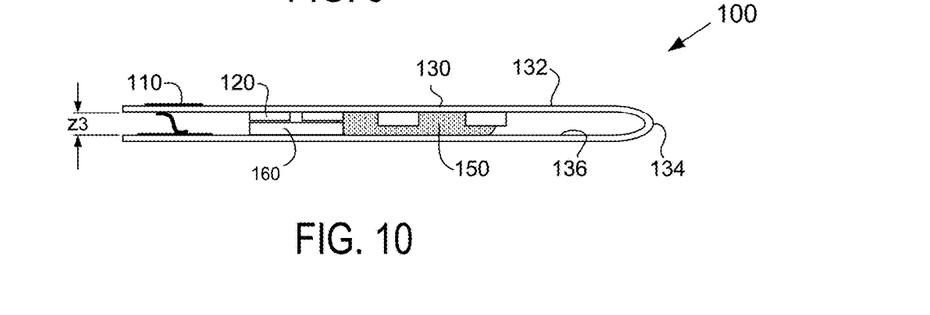
FIG. 10 is a side elevation view of a wearable electronic patch in a fully compressed state in accordance with various embodiments.

FIG. 10 illustrates a side elevation view of the wearable electronic patch 100 in a fully compressed state in accordance with various embodiments. In an embodiment, the wearable electronic patch 100 need not initially include some of the bulkier components, such as the battery 170. Without such bulky components, the wearable electronic patch 100 may be further compressed to a fully compressed state. In the fully compressed state, the z-height z3 is small. Temporary packaging, similar to that shown in FIG. 7 (e.g., 192, 196), may maintain the fully compressed state, which would have a smaller profile for the overall packaged device.

Figure 11:
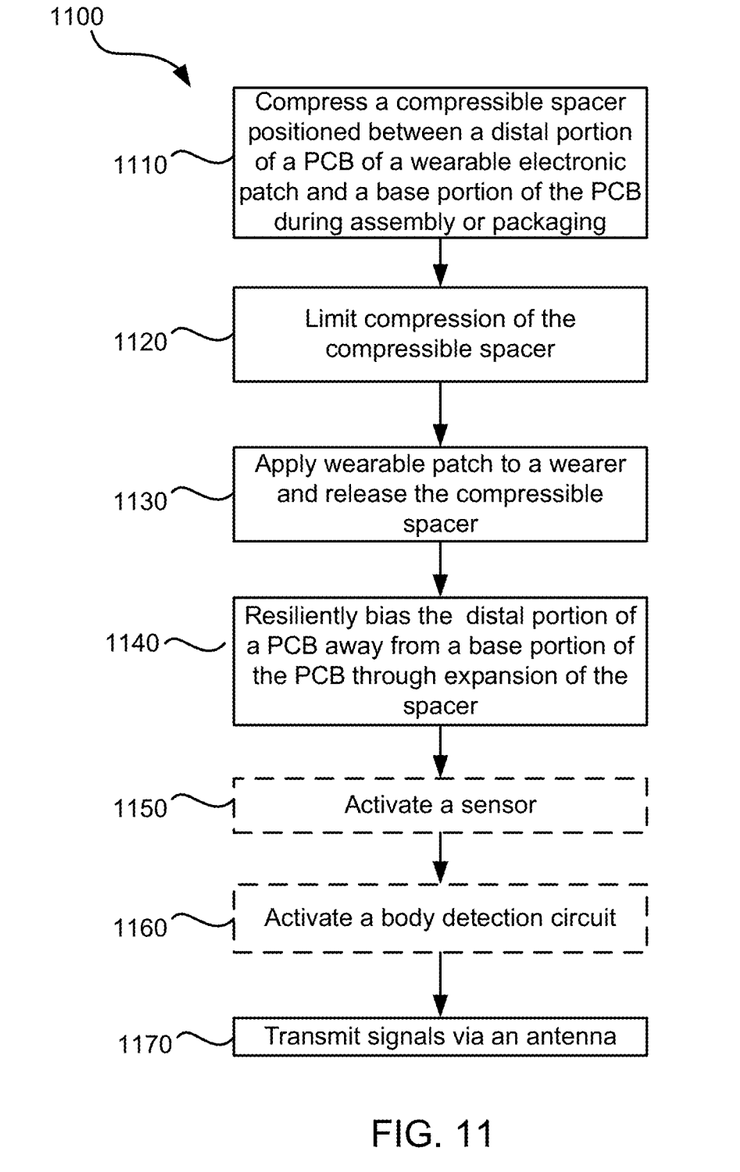
FIG. 11 is a process flow diagram illustrating a method of improving antenna gain of a wearable electronic patch when applied to a wearer in accordance with various embodiments.

FIG. 11 illustrates an embodiment method 1100 of making a wearable electronic patch for applying to a wearer, in accordance with various embodiments. The method 1100 may be performed using a wearable electronic patch similar to those described at least with reference to FIG. 1-10 (i.e., 100). In block 1110, a compressible spacer (e.g., 150) may be positioned between the distal portion and the base portion of a PCB of the wearable electronic patch. The distal portion may be spaced away from and opposed to the base portion that is configured to be closer to the wearer of the wearable electronic patch. Compressing the compressible spacer may resiliently bias the distal portion to expand away from the base portion. The compressible spacer may be compressed, such as during assembly of the wearable electronic patch. For example, the compressible spacer may be compressed as one of the final assembly steps to prepare the wearable electronic patch for packaging, or while placing the wearable electronic patch within when packaging. Compressing the compressible spacer may reduce the separation distance between the distal portion (e.g., 132) and the base portion (e.g., 136) of the printed circuit board (e.g., 130), and thus the overall thickness of the wearable electronic patch. Enabling the wearable electronic patch to be compressed to a thinner profile may enable the patch to be packaged and stored within less volume.

As described above, the amount to which the spacer may be compressed may be limited by in block 1120, such as based on a compression limit of the material forming the compressible spacer, or by a stop mechanism, such as a rigid structure configured to maintain space between the base portion and the antenna when the compressible spacer is not fully compressed.

In block 1130, the wearable electronic patch may be applied to a wearer (e.g., a patient) and as part of such application the compressible spacer (e.g., 150) may be released to allow the compressible spacer to expand from a compressed state (e.g., FIG. 7) to a lesser-compressed state (e.g., FIG. 9). Release of the compressible spacer may occur from the removal of packaging (e.g., 180), release of strap, or removal of a clip or clamp structure that maintains the compressible spacer in the compressed state.

In block 1140, releasing the compressible spacer (e.g., 150) so that it can expand may cause the distal portion (e.g., 132) of a printed circuit board (PCB, e.g., 130) of the wearable electronic patch (e.g., 100) to be resiliently biased away from a base portion (e.g., 136) of the printed circuit board (e.g., 130). This positions the antenna positioned on the distal portion so that it is spaced away from the body of the wearer in contact with the base portion of the wearable electronic patch. This separation between the antenna and the wearer's body may improve the antenna gain, and thus facilitate wireless communication links between the wearable electronic patch and another wireless communication device.

Optionally in block 1150, a sensor (e.g., 160) attached to at least one of the base portion (e.g., 136) and the distal portion (e.g., 132) of a printed circuit board (e.g., 130) may be activated. The sensor may be configured to measure one or more detectable physical characteristics of the wearer of the wearable electronic patch (e.g., 100).

Additionally or alternatively, a body detection circuit attached to the printed circuit board (e.g., 130) may be activated in block 1160. The body detection circuit may be a capacitive or thermal sensor configured to detect when the wearer is wearing the wearable electronic patch (e.g., 100).

In block 1170, the wearable electronic patch may transmit or receive radio signals via the antenna (e.g., 110) secured to the distal portion (e.g., 132).

Any reference to claim elements in the singular, for example, using the articles "a," "an" or "the" is not to be construed as limiting the element to the singular.

One skilled in the relevant art will recognize that many possible modifications and combinations of the aspects of the disclosed embodiments may be used, while still employing the same basic underlying mechanisms and methodologies. The foregoing description, for purposes of explanation, has been written with references to specific embodiments. However, the illustrative discussions above are not intended to be exhaustive or to limit the disclosure to the precise forms disclosed. Many modifications and variations are possible in view of the above teachings. The embodiments were chosen and described to explain the principles of the disclosure and their practical applications, and to enable others skilled in the art to best utilize the disclosure and various embodiments with various modifications as suited to the particular use contemplated. Thus, the present disclosure is not intended to be limited to the embodiments and individual aspects of the disclosed technologies shown and described herein, but is to be accorded the widest scope consistent with the following claims and the principles and novel features disclosed herein.

What is claimed is:

1. A wearable electronic patch for biological monitoring of a wearer, comprising: an antenna; a base portion having a first surface configured to face the wearer and a second surface is opposite the first surface of the base portion; a distal portion spaced away from and opposed to the base portion and having a first surface configured to face the second surface of the base portion, wherein the antenna is secured to the distal portion, wherein the base portion is configured to be closer to the wearer than the distal portion when the wearable electronic patch is worn by the wearer; an intermediate portion joining the base portion and the distal portion; and a spacer configured to be disposed between the second surface of the base portion and the first surface of the distal portion when the wearable electronic patch is worn by a wearer, wherein the spacer is sized and shaped to expand from a compressed state for moving the antenna away from the base portion.

2. The wearable electronic patch of claim 1, wherein when compressed the spacer maintains a space between the base portion and the antenna.

3. The wearable electronic patch of claim 1, wherein the spacer is formed of a foam material configured to expand after the base portion is secured to the wearer.

4. The wearable electronic patch of claim 1, wherein the spacer has a dielectric constant of approximately 1.0.

5. The wearable electronic patch of claim 1, wherein the base portion, the distal portion and the intermediate portion form a continuous printed circuit board.

6. The wearable electronic patch of claim 1, wherein a first end of the intermediate portion attached to the distal portion is folded over a second end of the intermediate portion attached to the base portion.

7. The wearable electronic patch of claim 1, further comprising an adhesive layer securing at least one of the base portion to the spacer and the spacer to the distal portion.

8. The wearable electronic patch of claim 1, wherein the antenna is a circuit element printed onto the distal portion.

9. The wearable electronic patch of claim 1, further comprising radio circuitry coupled to the antenna, wherein the radio circuitry is disposed between the base portion and the distal portion.

10. The wearable electronic patch of claim 1, further comprising a sensor attached to at least one of the base portion and the distal portion, wherein the sensor is configured to measure one or more physical characteristics.

11. The wearable electronic patch of claim 1, further comprising a body detection circuit configured to detect when the wearable electronic patch is worn by the wearer.

12. The wearable electronic patch of claim 1, further comprising a battery at least partially disposed between the base portion and the distal portion.

13. The wearable electronic patch of claim 1, further comprising a removable packaging covering at least one of the base portion and the distal portion, wherein removing of the packaging releases the spacer to expand from the compressed state.

14. The wearable electronic patch of claim 1, further comprising a permanent packaging encasing at least the base portion, the distal portion and the intermediate portion, wherein the permanent packaging is configured to expand in response to expansion of the spacer.

15. The wearable electronic patch of claim 1, further comprising a sensor coupled to the base portion, wherein the spacer is positioned and configured to separate the sensor from the antenna.

* * * * *